United States Patent [19]
Abrams et al.

[11] Patent Number: 5,472,447
[45] Date of Patent: Dec. 5, 1995

[54] POWER-ASSISTED OBTURATOR

[76] Inventors: Andrew L. Abrams, 26 Imperial Ave., Westport, Conn. 06880; Christopher M. Gaylo, 22 Landing La., Princeton Junction, N.J. 08550

[21] Appl. No.: 237,198

[22] Filed: May 3, 1994

[51] Int. Cl.$^6$ ............................................. A61B 17/34
[52] U.S. Cl. ..................... 606/169; 606/170; 606/171; 604/22; 604/164
[58] Field of Search .................... 604/22, 97, 22, 604/97, 164, 158; 128/660.1; 606/167, 169–171; 601/2

[56] References Cited

U.S. PATENT DOCUMENTS

| | | |
|---|---|---|
| 4,535,773 | 8/1985 | Yoon . |
| 4,674,498 | 6/1987 | Stasz ........................ 604/22 X |
| 4,931,047 | 6/1990 | Broadwin et al. ............ 604/22 |
| 5,116,353 | 5/1992 | Green . |
| 5,205,817 | 4/1993 | Idemoto et al. .............. 604/22 |
| 5,263,957 | 11/1993 | Davison .................. 604/22 X |
| 5,279,547 | 1/1994 | Costin ........................ 604/22 |
| 5,334,183 | 8/1994 | Wuchinch .............. 604/22 X |
| 5,344,420 | 9/1994 | Hilal et al. ............. 606/45 X |
| 5,359,996 | 11/1994 | Hood ......................... 604/22 |

FOREIGN PATENT DOCUMENTS 1098003  12/1977  Canada ..................... 604/22

*Primary Examiner*—Stephen C. Pellegrino
*Assistant Examiner*—Michael Peffley
*Attorney, Agent, or Firm*—Hayes, Soloway, Hennessey, Grossman & Hage

[57] ABSTRACT

A power-assisted obturator system for penetrating a body cavity wall is provided. The system comprises an obturator having main shank with a tip on its distal end. The tip has relatively blunt dull cutting edges which are incapable of readily cutting through bodily tissue except when the tip is vibrated at ultrasonic or near-ultrasonic frequencies. The proximal end of the main shank is connectable to an ultrasonic power source, which provides power to vibrate the obturator tip at ultrasonic or near-ultrasonic frequencies thereby transforming the relatively blunt edges into cutting edges which simultaneously cut and coagulate tissue. In a preferred embodiment, the obturator system includes vibration feedback and control which terminates delivery of energy to the tip when penetration is sensed.

11 Claims, 2 Drawing Sheets

POWER-ASSISTED OBTURATOR

FIELD OF THE INVENTION

Generally, the present invention relates to improvements in surgical systems, and more particularly to power-assisted surgical devices. The invention has particular utility in connection with ultrasonic powered obturators and will be described in connection with such utility, although other utilities are contemplated.

BACKGROUND OF THE INVENTION

In recent years less invasive surgery (e.g., laparoscopic surgery) has become the standard method for performing several common procedures, e.g. a cholecystectomy. These procedures are generally performed by inserting a trocar casing through a body cavity wall to gain access to a body cavity or region. The trocar casing is used as an access port for the introduction of instruments to provide visualization and to operate upon organs within the cavity.

In order to penetrate the body cavity wall through which the trocar casing is to pass, an obturator is fitted within the tube of the trocar. Obturators typically comprise a main shank with a solid metal tip having three sharp edges at its distal end. The tip of the obturator is manually forced through the body wall to create an opening through which the trocar casing may pass. Typically, the surgeon must apply considerable force to the proximal end of the obturator to cause the tip to penetrate the soft body tissue, i.e. skin-fat-muscle-peritoneal layers of the body cavity wall. Once the wall is penetrated, however, there is an abrupt drop in penetration resistance. Typically, the surgeon may not be able to respond fast enough to avoid over-insertion, with the result that the sharp obturator tip may be thrust into the body cavity, potentially causing injury to the organs or vessels contained therein.

In addition to the inherent danger of damaging tissue within a body cavity as a result of over-insertion, current obturator structures may cause significant bleeding in a body cavity wall upon penetration. This bleeding can cloud the area to be operated upon, and thereby reduce the surgeon's view through visualization optics carried within the trocar casing. Accordingly, once the body cavity wall has been penetrated by the obturator tip, the resulting bleeding must be stopped, or the blood cleared away before the operation can be safely performed. These steps may prolong the surgical procedure and result in increased patient discomfort.

In an attempt to address the problem associated with obturator over-insertion, the prior art has proposed several solutions. For example, Green, U.S. Pat. No. 5,116,353 teaches a safety trocar structure wherein the cutting tip of the obturator is withdrawn into the cannula of the trocar casing in response to a counterforce being removed from the the cutting tip. The cutting tip is maintained in an exposed position as the surgeon forces the tip against the body cavity wall; however, when the tip penetrates the body cavity wall it is automatically withdrawn into the cannula under the force of a spring.

Even in devices such as taught by Green, inadvertent patient injury can still occur when the force to penetrate the body wall suddenly drops upon entry into the cavity. Typically, a surgeon is unable to predict and accurately control the force required to penetrate the wall. If too great a force is asserted, a device such as that taught by Green may not react fast enough to withdraw the sharp tip of the obturator into the trocar cannula. In addition, while the tip may retract, the entire trocar tube may be overinserted potentially injuring the patient. Also, the possibility of mechanical failure caused by repeated use presents an inherent potential for injury from the sharp edges of the obturator tip.

In addition to the potential for injury caused by overinsertion that persists in prior art obturator structures, the prior art has failed to address the problems associated with the bleeding of the body cavity wall upon penetration. As a result, existing obturator devices continue to suffer from the disadvantages cited above, thereby decreasing the overall safety, efficiency and patient comfort in commonly performed less invasive surgical procedures.

SUMMARY OF THE INVENTION

There is thus provided in accordance with one aspect of the present invention a power-assisted obturator system which eliminates the potential for injury resulting from over insertion by providing controllable power assist to the surgeon in penetrating a body cavity wall. In addition, the obturator system of the present invention provides hemostasis of the tissue during penetration whereby to reduce or avoid bleeding.

The power-assisted obturator system of the present invention comprises a hand-held instrument having a main shank with a tip attached to its distal end. The tip has cutting edges which are relatively blunt or rounded as compared to the sharp cutting edges of conventional obturators, so as not to cut through body tissue under normal manual insertion forces. However, the edges are sufficiently well defined so that when the tip is vibrated at ultrasonic or near-ultrasonic frequencies, the tip readily will cut through body tissue. Completing the system are means for connecting a power generator such as an ultrasonic energy source to the proximal end of the main shank, for vibrating the tip at ultrasonic or near-ultrasonic frequencies.

With the tip in an active vibrational state, the relatively blunt edges of the tip are capable of penetrating into and through soft body tissue with minimal manual insertion force. Moreover, due to the ultrasonic or near-ultrasonic vibration of the cutting edges, hemostasis occurs along the cutting tract simultaneous with penetration of the tissue. Accordingly, the disadvantages associated with blood entering the body cavity and obscuring the target area are essentially eliminated.

The power-assisted generator also preferably comprises means for controlling the frequency amplitude and wave shape at which the obturator tip vibrates. By controlling the vibration frequency amplitude and wave form, the surgeon can increase or decrease the amount of force required or rate at which the trocar passes through the body cavity wall, and thereby avoid the unpredictable point where there is a sudden drop in penetration resistance when the tip passes through the body cavity wall. Also, in a preferred embodiment of the invention, means are provided for sensing penetration and for automatically turning off the vibration energy being supplied to the tip once the vibrating tip has cut through the body cavity wall.

BRIEF DESCRIPTION OF THE DRAWINGS

Other aspects, features, and utilities of the present invention will become apparent as the following description proceeds, and upon reference to the hereinafter appended drawings wherein like numerals represent like parts, and wherein.

While the present invention will hereinafter be described in connection with a preferred embodiment and method use it will be understood that it is not intended to limit the invention to this embodiment or method of use. On the contrary, it is intended to cover all alternatives, modifications and equivalents as may be included within the spirit and broad scope of the invention as defined by the hereinafter appended claims.

DESCRIPTION OF THE PREFERRED EMBODIMENTS

Figure 1:
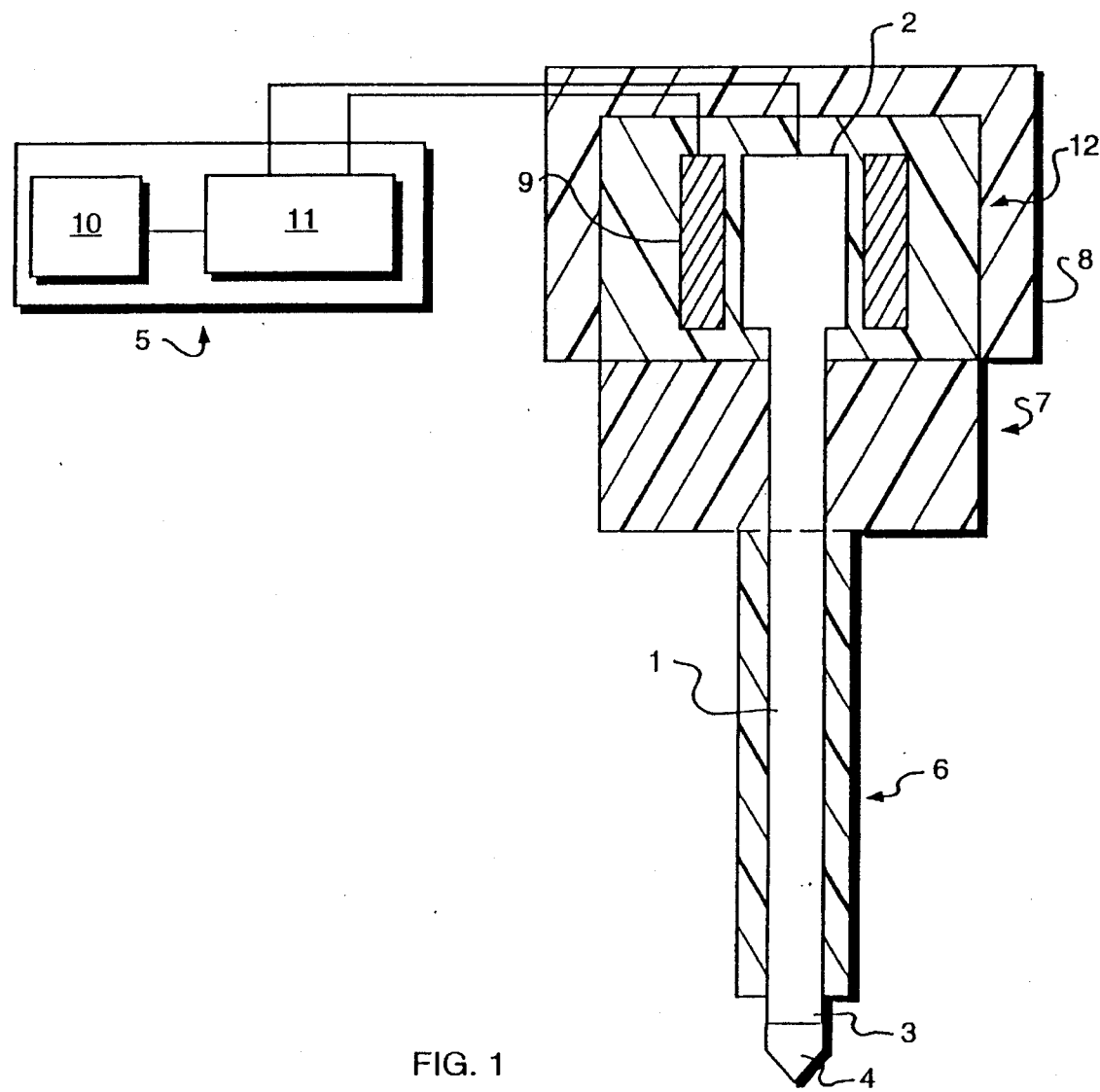
FIG. 1 is a side-sectional view of the preferred embodiment of a power-assisted obturator system made in accordance with the present invention.

FIG. 1 shows in side-sectional view, a preferred form of power-assisted obturator system made in accordance with the present invention. The system comprises an obturator having main shank 1 with a proximal end 2 and distal end 3. The main shank 1 is fitted within a standard trocar tube 6. The trocar tube 6 is connected to a trocar housing and seal assembly 7 which acts as an access port for surgical instruments once the trocar tube is passed into a body cavity.

Connected to the proximal end 2 of the obturator main shank is a coil or actuator assembly 12 containing a coil or actuator 9 which provides vibrational energy input i.e. at ultrasonic or near-ultrasonic frequencies, to the obturator tip 4 through the main shank 1. The coil or actuator assembly 12 is encased in housing 8. The proximal end 2 of the obturator main shank 1 is freely movable within the coil or actuator assembly 12. The detailed method by which the obturator tip is induced to vibrate at ultrasonic or near ultrasonic frequencies can take a variety of forms.

A power generator 5 is connected to the coil or actuator 9 to generate the ultrasonic or near ultrasonic vibrational energy, e.g. by means of piezoelectric, magnetostrictive, pulsed solenoid action or other means, to vibrate the obturator tip 4. Contained within the power generator 5 is a control unit 10 through which the surgeon may control the frequency amplitude and/or wave form at which the tip 4 vibrates. By controlling the frequency amplitude and/or wave form, the surgeon can control the rate and force required to cause the obturator tip 4 to penetrate through a body cavity wall under normal manual insertion forces.

A vibration feedback and control circuit 11 monitors the frequency amplitude and/or wave form at which the distal end 3 of the obturator main shank is vibrating, and senses when the obturator tip 4 passes through the body cavity wall into the body cavity by sensing a change in the frequency amplitude and/or wave form at which the tip is vibrating. When this change is sensed by the resonance feedback circuit, the circuit switches off the power supplied by the generator 5 to the coil or actuator 9 thereby stopping the ultrasonic vibration of the obturator tip 4. The sensor may be located anywhere along the main shank 1, from the distal end 3 to proximal end 2.

Figure 3:
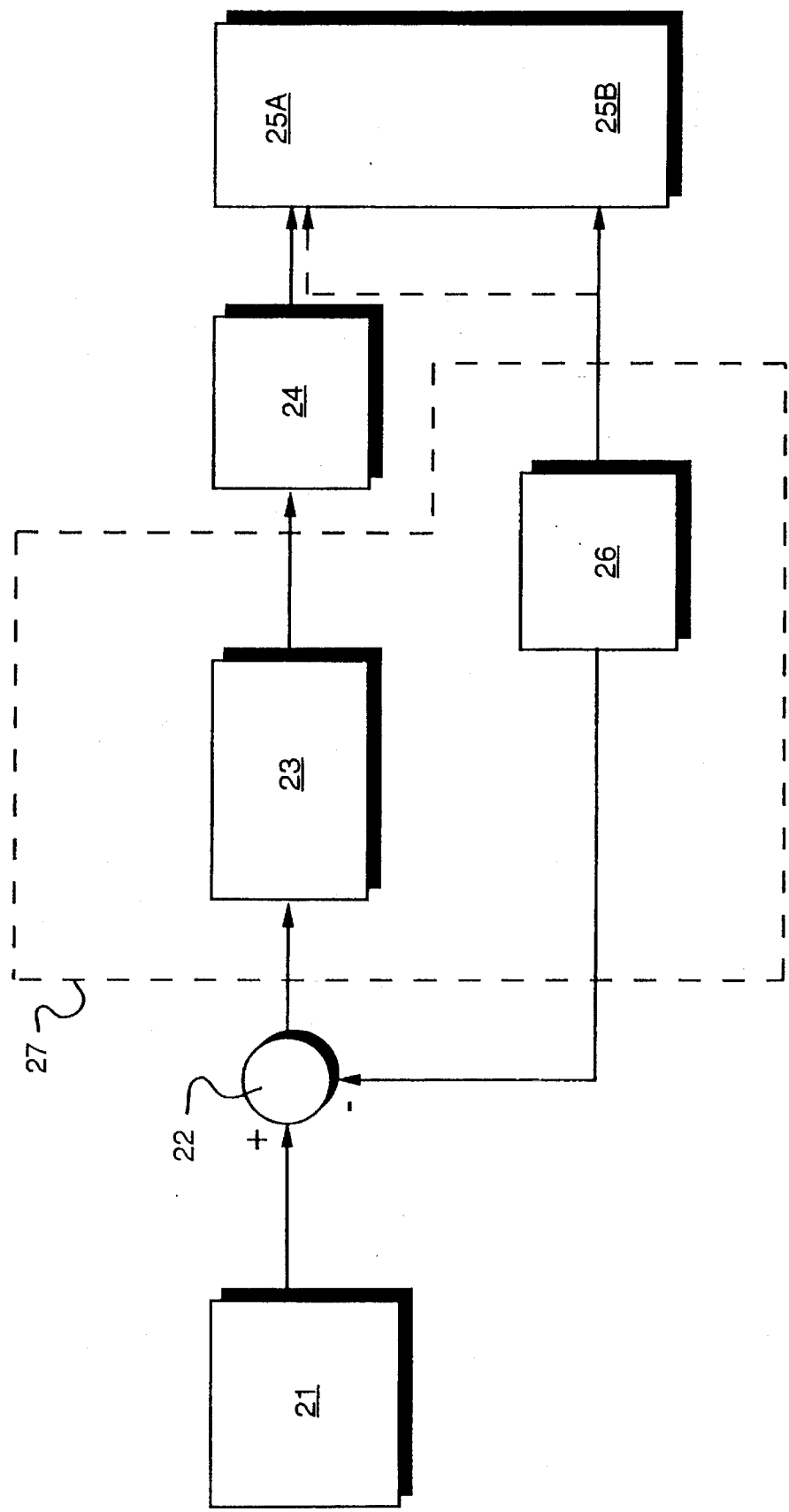
FIG. 3 is a block flow diagram of a vibration feedback and control system in accordance with a preferred embodiment of the present invention.

More particularly, referring to FIG. 3, a preferred embodiment of the vibration feedback and control circuit 27 comprises a sensor 26 and comparator circuitry 23. The sensor 26 constantly monitors the frequency amplitude and/or wave form or other characteristic at which the distal end 25B of the obturator main shank is vibrating, and provides an output to the summation point 22 which indicates the operating state of the obturator tip. The sensor output is combined at the summation point 22 with the output of the power generator control unit 21. The control unit output is a signal proportional to the desired vibration frequency, and is set by the surgeon. The signal at the summation point 22 acts as the input to the comparator circuitry 23 which provides the driving signal for the coil or actuator 24. The coil or actuator 24 directly causes the vibration of the proximal end of the obturator main shank 25A.

In operation, the vibration feedback and control circuit 27 acts to maintain the constant obturator tip vibration conditions set by the surgeon thereby providing a controllable cutting rate and consistent hemostasis. As the surgeon touches the obturator tip against a body cavity wall, friction and mechanical coupling between body tissue and the tip changes the vibration characteristics of the tip. The sensor 26 responds to this change by changing its output. As described above, the sensor output combines with the control unit output at summation point 22 and the resulting signal is provided at the input to the comparator circuitry 23. The comparator circuitry 23 is designed to compare its current input, with its current output. If the current input would result in a higher output to the coil or actuator circuit 24 than that which is is currently provided, then the comparator circuitry would use its current input to generate an increased output to the coil or actuator. As a result, the coil or actuator output increases thereby overcoming the change in vibration characteristic caused by the friction and mechanical coupling between the tissue and the obturator tip. In this way, vibration is held constant by the vibration feedback control circuit as the tip passes through the body cavity wall.

When the tip passes through the wall, however, the friction and mechanical coupling between the tip and the tissue is removed and the vibration characteristic changes, tending to increase due to the increased input signal provided to the coil or actuator in response to the previous friction and/or coupling. When this occurs, the vibration sensor output is reduced causing a reduction of the input to the comparator circuitry. The comparator circuitry compares its current input with its current output, and determines that the input would result in an output which is lower than that which currently exists. In this situation, the comparator circuit 23 is designed to completely disable its output to the coil or actuator circuitry 24. Accordingly, the actuator turns off, and the vibration of the tip is terminated. Thus, in the preferred embodiment, the vibration feedback and control circuit maintains a constant tip vibration condition as long as there is a constant or increasing penetration resistance. However, once there is a significant drop in penetration resistance, i.e. the tip passes into the body cavity, the vibration is terminated and the tip is no longer capable of readily cutting bodily tissue.

Referring again to FIG. 1, after the body cavity wall is penetrated by the obturator tip, the trocar tube 6 may be passed into the body cavity and the housing 8, containing the coil or actuator assembly 12 and the obturator, is removed from the trocar tube 6 and seal assembly 7. The trocar tube is left inserted in the body cavity, and the seal assembly acts as an access port to the cavity for visualization and surgical instruments.

Figure 2:
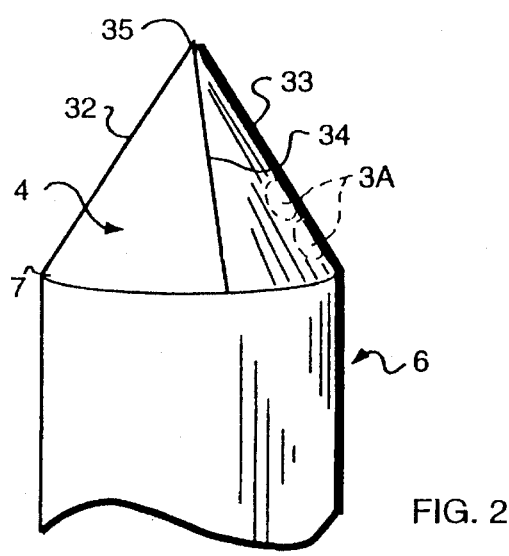
FIG. 2 is a side-view of a preferred embodiment of an obturator tip made in accordance with the present invention.

Referring now to FIG. 2, a side-view of a preferred embodiment of an obturator tip made in accordance with the present invention is depicted. The obturator tip 4 contains two or more relatively blunt or rounded edges. In a preferred embodiment there are three edges, 32, 33, and 34, each of which extends from a common point 35 back to the main shank. The tip may be integral with or detachable from the shank 6. In the latter case, the tip and the main shank may be formed of different materials. The tip 4 contacts the distal end of the main shank at 7 where, in the preferred embodiment, each of the edges 32, 33, and 34 are located approximately 120 degrees from one another around the shank. The tip edges 32, 33 and 34 may be made straight edged or have contoured shape and may consist of multiple edges, e.g. scallops as shown in broken lines at 3A, spaced at the same or different angles from one another. The edges 32, 33 and 34 are made relatively blunt or rounded, i.e. as compared to the sharp edges of conventional obturator tips, and thus are unable to passively cut through tissue under normal manual insertion forces. However, the tip edges 32, 33 and 34 are sufficiently defined so that when induced to vibrate at ultrasonic or near ultrasonic frequencies, the edges act as energy concentrators, so as to penetrate and coagulate tissue simultaneously under only minimal manual insertion forces.

A preferred method of using the power-assisted obturator system made according to the present invention will now be described. First, the obturator main shank 6 with the tip 4 attached to its distal end 3 is inserted into the trocar tube. The housing 8, containing the coil or actuator assembly 12 and the proximal end 2 of obturator, is placed adjacent to the trocar seal assembly 7 as shown in FIG. 1. The obturator tip is then extended beyond the distal end of the trocar tube 6 and positioned adjacent a body cavity wall to be penetrated. The surgeon then turns on the power generator 5 which sets the obturator tip 4 vibrating at ultrasonic or near-ultrasonic frequency so that the tip 4 may penetrate and pass through the body cavity wall under only minimal application of manual insertion forces. Simultaneous coagulation of the body cavity tissue occurs along the cutting tract as the vibrating tip 4 passes through the body cavity wall. When the tip penetrates through the body cavity wall, the vibration feedback and control circuitry 11 senses a change in the uniform ultrasonic or near-ultrasonic frequency characteristics at which the tip is vibrating, and automatically turns off the ultrasonic power generator 5 whereby the tip stops vibrating. Since the tip is no longer vibrating at ultrasonic or near-ultrasonic frequencies, the blunt edges of the tip present no danger of injury to tissue within the cavity. In addition, the low and controlled manual insertion forces minimizes the potential for overinsertion. Finally, the surgeon extends the trocar casing 6 into the body cavity and removes the housing encasing and obturator from the trocar. The distal end of the trocar tube is left in the body cavity, and the seal assembly 7, which remains outside of the body, acts as an access port to the body cavity for visualization and surgical instruments.

It is evident that there has been provided, in accordance with the present invention, a unique power-assisted obturator system for penetrating a body cavity wall. While this invention has been described in conjunction with a specific embodiment thereof, various alternatives and modifications may be made without departing from the spirit and scope of the invention. Accordingly, it is intended to embrace all such alternatives, modifications, and variations that fall within the spirit and broad scope of the hereinafter appended claims.

What is claimed is:

1. A power-assisted obturator comprising:

an elongate obturator having a main shank with a proximal and a distal end;

an obturator tip on said distal end, said tip having multiple relatively blunt cutting edges which are incapable of readily cutting through a body cavity wall except when said tip is vibrated at ultrasonic or near-ultrasonic frequencies;

means for connecting the proximal end to a power generator for vibrating said tip at said frequencies; and wherein, said power generator includes control and feedback means for adjusting vibration characteristics of said tip while said tip is within said cavity wall so as to keep cutting capabilities of said tip substantially constant while said tip is within said cavity wall, and said control and feedback means includes means for sensing changes in the frequency at which said tip vibrates when said tip has penetrated through said body cavity wall and means for automatically terminating vibration of said tip upon penetration.

2. A power-assisted obturator according to claim 1, wherein said tip has three cutting edges which extend from a common point back to the distal end of the main shank, each one of said edges being spaced approximately 120 degrees from another around said shank.

3. A power-assisted obturator according to claim 1, wherein said obturator is carried within an elongate trocar casing and is slidably movable within said trocar casing.

4. A power-assisted obturator according to claim 1, wherein the tip is detachable from the main shank.

5. A power-assisted obturator according to claim 4 wherein the tip and the main shank are formed of different materials.

6. A power-assisted obturator according to claim 1 wherein the cutting edges of the tip have a contoured shape comprising a multiple of edges spaced from one another.

7. A power-assisted obturator according to claim 1, wherein said vibration characteristics include vibration frequency characteristics.

8. A power-assisted obturator according to claim 1, wherein said control and feedback means comprises a control unit for selecting desired vibration characteristics of said tip, a sensor for determining actual vibration characteristics of said tip, means for determining differences between said desired and said actual characteristics, and means for adjusting vibration of said tip based upon said differences.

9. A power-assisted obturator according to claim 1, wherein said vibration characteristics include vibration amplitude characteristics.

10. A power-assisted obturator according to claim 1, wherein said vibration characteristics include vibration wave form characteristics.

11. A power-assisted obturator according to claim 1, wherein said vibration characteristics change as a function of penetration resistance of said body cavity wall to said tip.

\* \* \* \* \*